United States Patent
Ochoa

(10) Patent No.: US 10,690,127 B2
(45) Date of Patent: Jun. 23, 2020

(54) HANDHELD OPHTHALMIC PROBE WITH PERISTALTIC PUMP AND ASSOCIATED DEVICES, SYSTEMS, AND METHODS

(71) Applicant: Novartis AG, Basel (CH)

(72) Inventor: Francisco Javier Ochoa, Cudahy, CA (US)

(73) Assignee: Alcon Inc., Fribourg (CH)

( * ) Notice: Subject to any disclaimer, the term of this patent is extended or adjusted under 35 U.S.C. 154(b) by 437 days.

(21) Appl. No.: 15/253,046

(22) Filed: Aug. 31, 2016

(65) Prior Publication Data

US 2018/0058438 A1 Mar. 1, 2018

Related U.S. Application Data

(60) Provisional application No. 62/381,455, filed on Aug. 30, 2016.

(51) Int. Cl.
| | |
|---|---|
| *F04B 43/12* | (2006.01) |
| *A61M 1/00* | (2006.01) |
| *A61F 9/007* | (2006.01) |
| *F04B 49/20* | (2006.01) |

(52) U.S. Cl.
CPC ...... *F04B 43/1269* (2013.01); *A61F 9/00736* (2013.01); *A61F 9/00745* (2013.01); *A61M 1/0023* (2013.01); *A61M 1/0037* (2013.01); *A61M 1/0058* (2013.01); *A61M 1/0072* (2014.02); *F04B 43/1261* (2013.01); *F04B 49/20* (2013.01); *A61M 2210/0612* (2013.01); *F05B 2250/241* (2013.01); *F05B 2280/1071* (2013.01); *F05B 2280/401* (2013.01)

(58) Field of Classification Search
CPC ............ A61F 9/00736; A61F 9/00745; A61M 1/0072; A61M 1/0023; A61M 1/0037; F04B 43/1269; F04B 43/1261; F04B 49/20
See application file for complete search history.

(56) References Cited

U.S. PATENT DOCUMENTS

| | | | | |
|---|---|---|---|---|
| 4,417,856 | A * | 11/1983 | Minissian | ........... F04B 43/1276 |
| | | | | 417/477.7 |
| 4,465,470 | A * | 8/1984 | Kelman | .............. A61F 9/00736 |
| | | | | 604/27 |

(Continued)

FOREIGN PATENT DOCUMENTS

EP    1662142 A1    5/2006

*Primary Examiner* — Ariana Zimbouski

(57) ABSTRACT

Systems, apparatuses, and methods of and for an ophthalmic surgical system are disclosed. An ophthalmic surgical system may include a handheld probe. The probe may include a housing sized and shaped for grasping by a user. The probe may include a tip extending from the housing and being sized to penetrate and treat an eye of a patient. The tip may include an aspiration lumen arranged to carry fluid away from the eye. The probe may include a peristaltic pump disposed within the housing. The pump may include a roller in contact with a deformable conduit in fluid communication with the aspiration lumen. The roller may be arranged to deform the conduit while in contact therewith. The pump may also include a roller driver in contact with a periphery of the roller in a manner that moves the roller along the conduit to urge the fluid through the conduit.

11 Claims, 11 Drawing Sheets

(56) References Cited

U.S. PATENT DOCUMENTS

| | | | | |
|---|---|---|---|---|
| 4,817,599 | A | * | 4/1989 | Drews .................. A61F 9/00745 604/151 |
| 5,840,069 | A | * | 11/1998 | Robinson ............ F04B 43/1269 604/131 |
| 9,291,159 | B2 | | 3/2016 | Baxter |
| 2007/0270735 | A1 | | 11/2007 | Williams |
| 2007/0270746 | A1 | | 11/2007 | King |
| 2007/0282262 | A1 | | 12/2007 | King |
| 2008/0146988 | A1 | | 6/2008 | Olivera |
| 2008/0149197 | A1 | | 6/2008 | Olivera |
| 2008/0168985 | A1 | | 7/2008 | Turner |
| 2012/0282126 | A1 | * | 11/2012 | Brandt .................. F04B 43/082 417/477.9 |
| 2014/0213993 | A1 | | 7/2014 | Kuebler |
| 2014/0271273 | A1 | | 9/2014 | Carpenter |
| 2014/0356202 | A1 | | 12/2014 | Hashemi |
| 2014/0356203 | A1 | | 12/2014 | Baxter |
| 2014/0356204 | A1 | | 12/2014 | Sorensen |
| 2014/0356206 | A1 | | 12/2014 | Hashemi |

* cited by examiner

HANDHELD OPHTHALMIC PROBE WITH PERISTALTIC PUMP AND ASSOCIATED DEVICES, SYSTEMS, AND METHODS

CROSS-REFERENCE TO RELATED APPLICATIONS

This application claims the benefit of U.S. Provisional Application No. 62/381,455, filed Aug. 30, 2016, the entire contents of which is incorporated herein by reference.

TECHNICAL FIELD

The present disclosure is directed to ophthalmic surgical devices, systems, and methods. More particularly, but not by way of limitation, the present disclosure is directed to handheld probes having a peristaltic pump.

BACKGROUND

The human eye provides vision by transmitting light through a clear outer portion called the cornea, and focusing the image by way of a crystalline lens onto a retina. The quality of the focused image depends on many factors including the size and shape of the eye and the transparency of the cornea and the lens. When age or disease causes the lens to become less transparent, vision deteriorates because of the diminished light that can be transmitted to the retina. This deficiency in the lens of the eye is medically known as a cataract. An accepted treatment for this condition is surgical removal of the lens and replacement of the lens function by an artificial intraocular lens (TOL).

Cataractous lenses may be removed using a surgical technique called phacoemulsification. A typical surgical probe used in phacoemulsification procedures includes a handpiece or handheld probe having an ultrasonically driven cutting needle. During the procedure, a surgeon brings the tip of the cutting needle into contact with the lens of the eye. The cutting needle rapidly vibrates such that contact with tip fragments the lens. Throughout the procedure, irrigating fluid is delivered into the eye. Fluid including the lens fragments is also aspirated out of the eye. In some instances, the cutting needle includes an aspiration lumen through which the fluid is aspirated. The fluid may be aspirated from the eye, through the aspiration lumen, through elastic tubing, and to a drain reservoir.

A common phenomenon during a phacoemulsification procedure arises from a blockage, or occlusion, of the aspiration lumen. As the irrigation fluid and lens fragments are aspirated away from the interior of the eye through the aspiration lumen of the cutting needle, pieces of tissue that are larger than the diameter of the aspiration lumen may occlude or clog the aspiration lumen, particularly at the opening of the aspiration lumen at the tip of the cutting needle. While the aspiration lumen is clogged, vacuum pressure builds up, causing collapse of the elastic tubing. When occlusion is cleared, an undesirably large quantity of fluid and tissue may be drawn from the eye into the aspiration lumen too quickly. This is known as post-occlusion surge. The post-occlusion surge can, in some cases, cause the eye to collapse and/or the lens capsule to be torn.

SUMMARY

The present disclosure describes example ophthalmic surgical systems that may include a handheld probe. The probe may include a housing sized and shaped for grasping by a user. The probe may also include a tip extending from the housing and being sized to penetrate and treat an eye of a patient. The tip may include an aspiration lumen arranged to carry fluid away from the eye. The probe may also include a peristaltic pump disposed within the housing. The pump may include a deformable conduit comprising a conduit lumen extending therethrough. The conduit lumen may be in fluid communication with the aspiration lumen. The pump may also include a roller in contact with the deformable conduit and include an outer peripheral surface. The roller may be engaged with the deformable conduit to cause the deformable tubing to deform. The pump may also include a roller driver in contact with an outer peripheral surface of the roller. The roller may be movable along the deformable conduit in response to movement of the roller driver to cause movement of material within the conduit lumen therealong.

The present disclosure may also disclose ophthalmic surgical systems that may include a handheld probe. The handheld probe may include a housing sized and shaped for grasping by a user, a tip extending from the housing and being sized to penetrate an eye, and a peristaltic pump disposed within the housing. The tip may include a tip lumen arranged to carry fluid. The pump may include a deformable conduit defining a conduit lumen. The conduit lumen may be in fluid communication with the tip lumen. The pump may also include a plurality of rollers in contact with the deformable conduit. The plurality of rollers may form localized deformation in the deformable conduit. Each of the plurality of rollers may include an outer peripheral surface. The pump may also include a roller driver in contact with the outer peripheral surface of each roller of the plurality of rollers. The plurality of rollers may be moveable in response to movement of the roller driver to transport material within the conduit lumen therealong. The probe may also include a motor disposed within the housing. The motor may include a motor shaft coupled to the roller driver. The roller driver may be moveable in response to movement of the motor shaft.

In addition, the present disclosure is directed to ophthalmic surgical methods. An exemplary method may include inserting a tip of a surgical probe into an eye of a patient. The tip may include an aspiration lumen arranged to carry material away from the eye. The method may also include contacting a plurality of rollers with a deformable conduit to cause localized deformation of the deformable conduit by each of the plurality of rollers; engaging an outer peripheral surface of each of the plurality of rollers by a roller driver; and aspirating material from the eye by moving the roller driver to cause movement of the plurality of rollers along the deformable conduit to peristaltically pump material contained within a lumen of the deformable conduit.

In different implementations, the various aspects of the disclosure may include one or more of the following features. A roller driver may not include an axle extending through the roller. The peristaltic pump may include a plurality of rollers arranged in a circular configuration. The plurality of rollers may be in contact with the deformable conduit and disposed between the deformable conduit and the roller driver. The roller driver may include a surface in contact with the plurality of rollers. The peristaltic pump further may include a track housing defining a channel. The channel may define a track along which the plurality of rollers travels. The deformable conduit may be positioned within the channel, and the plurality of rollers may be arranged to move along the track while in contact with the deformable conduit and the roller driver. The track may include a contact surface that limits deformation of the deformable conduit by limiting movement of the plurality of rollers into the channel. The peristaltic pump may also include a guide member having a plurality of recesses. Each of the plurality of rollers may be positioned in a respective one of the plurality of recesses. The probe may also include a motor disposed within the housing. The motor may include a motor shaft coupled to the roller driver. The motor may rotate the roller driver. A roller may be spherical. The deformable conduit may include a first segment carrying the material in a first direction and a second segment carrying the material in a second direction.

A controller may be operable to transmit a control signal to the motor to increase and decrease a speed of the motor. A drain reservoir may be in fluid communication with the deformable conduit. Material transported within the conduit lumen may be deposited in the drain reservoir. The handheld probe may be a phacoemulsification probe.

The roller driver may be coupled to a motor disposed within the surgical probe, and the motor may include a motor shaft coupled to the roller driver. The deformable conduit may be disposed within a channel formed in a track housing, and the plurality of rollers may be moved along a track formed by the channel.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

Figure 1:
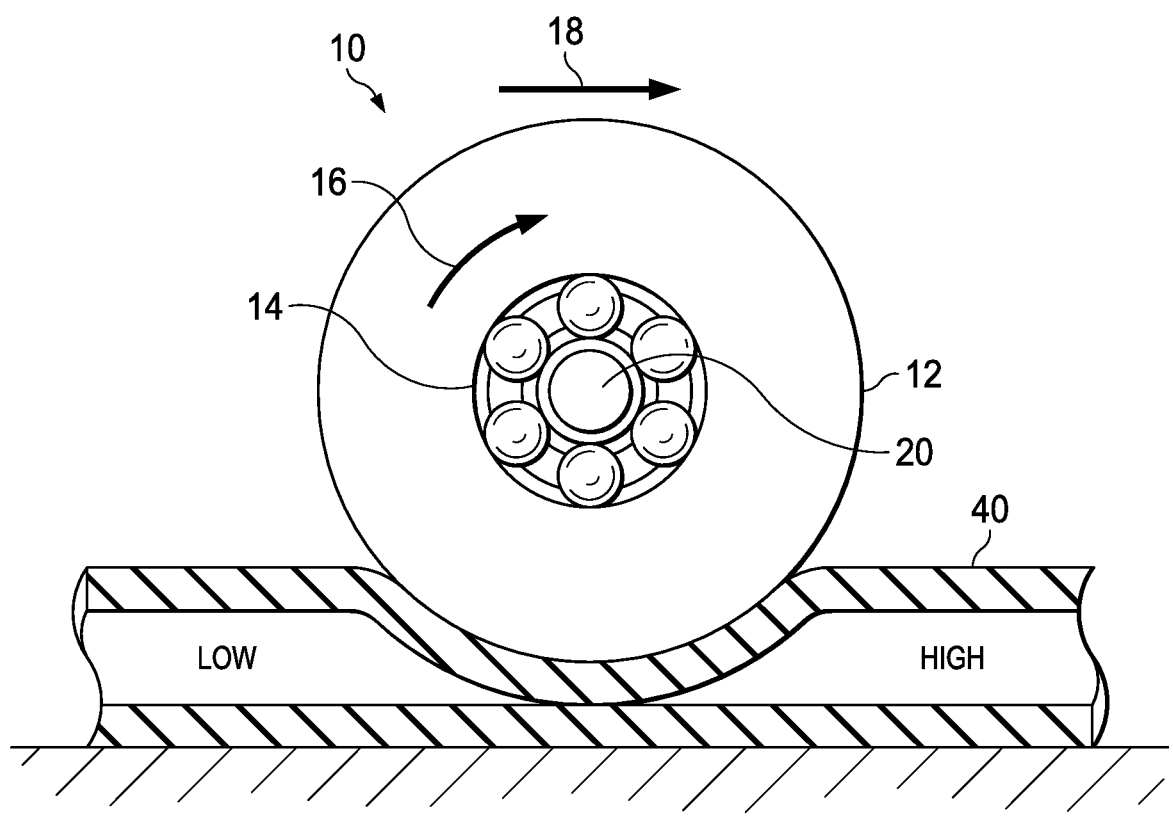
FIG. 1 is an illustration of a conventional peristaltic pump.

These figures will be better understood by reference to the following detailed description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure relates generally to devices, systems, and methods for aspirating materials, such as fluid, lens particles, other materials, including other biological materials, or a combination thereof, from the eye using a peristaltic pump. In some implementations, the pump is arranged to be fit within a handheld surgical probe, such as a phacoemulsification probe. The pump includes one or more rollers in contact with a flexible/deformable conduit through which the aspiration fluid flows. The pump also includes a roller driver that is in contact with peripheries or outer surfaces of the rollers. For example, the roller driver may be a rotating plate or a rotating cylinder having a surface that frictionally engages and moves the rollers. The roller driver moves the rollers along the conduit to urge the fluid to flow. Conventional peristaltic pumps are discussed more below with reference to FIG. 1.

FIG. 1 shows a conventional pump 10 utilizing a roller 12 to move along the tubing 40 in a direction 18. The roller 12 may be driven by a motor. Friction between the roller 12 and the tubing 40 causes the roller 12 to rotate about an axle 20 in a direction 16. The axle 20 translates in the direction 18 as the roller 12 moves along the tubing 40 in the direction 18. The roller 12 contacts and deforms the tubing 40, creating regions of high pressure and low pressure within the tubing 40 on either side of the roller 12. The high pressure and low pressure regions move along the tubing 40 as the roller 12 moves along the tubing 40 in the direction 18. The rollers 12 peristaltically move material within the tubing 40 in the direction 18 as the rollers 12 move in the direction 18.

In such pumping mechanisms, high friction may occur between the roller 12 and the axle 20 about which the roller 12 rotates. Overcoming this friction may complicate design and manufacturing of the phacoemulsification probe. Additional components, such as a bearing 14, may need to be added to the pump 10 to minimize the roller-axle friction. A motor with a relatively greater power output to overcome the friction can be used to operate the pump 10. However, such a motor may be too large, too heavy, and/or too expensive to implement in the phacoemulsification probe. Peristaltic pumping mechanisms of a type as shown in FIG. 1 may involve high friction between the elastic tubing and a component that contacts the tubing. As a result, the probe may require additional lubrication components and/or a more powerful motor to overcome the friction.

However, unlike conventional systems, the peristaltic pumps described herein do not include an axle extending through the rollers. For example, a motor shaft of a motor may be coupled to the roller driver as opposed to the rollers via an axle extending therethrough.

The devices, systems, and methods of the present disclosure provide numerous advantages over conventional aspiration pumps. For example, the arrangement of the pump described herein minimizes friction resulting from interaction between the axle and the roller because no axle is utilized. Because friction effects can dominate system dynamics at smaller scales, minimizing friction makes the pump more amenable to miniaturization. A smaller pump can be implemented within a surgical probe, which advantageously reduces or eliminates post-occlusion surge effects. Smaller, lighter, and/or less expensive motors can be used to drive a pump with less friction. Omitting the axle also minimizes the need for lubrication. Some implementations of the pump described herein also utilize rollers having a simple geometry, which may allow for a simple pump design.

Figure 2:
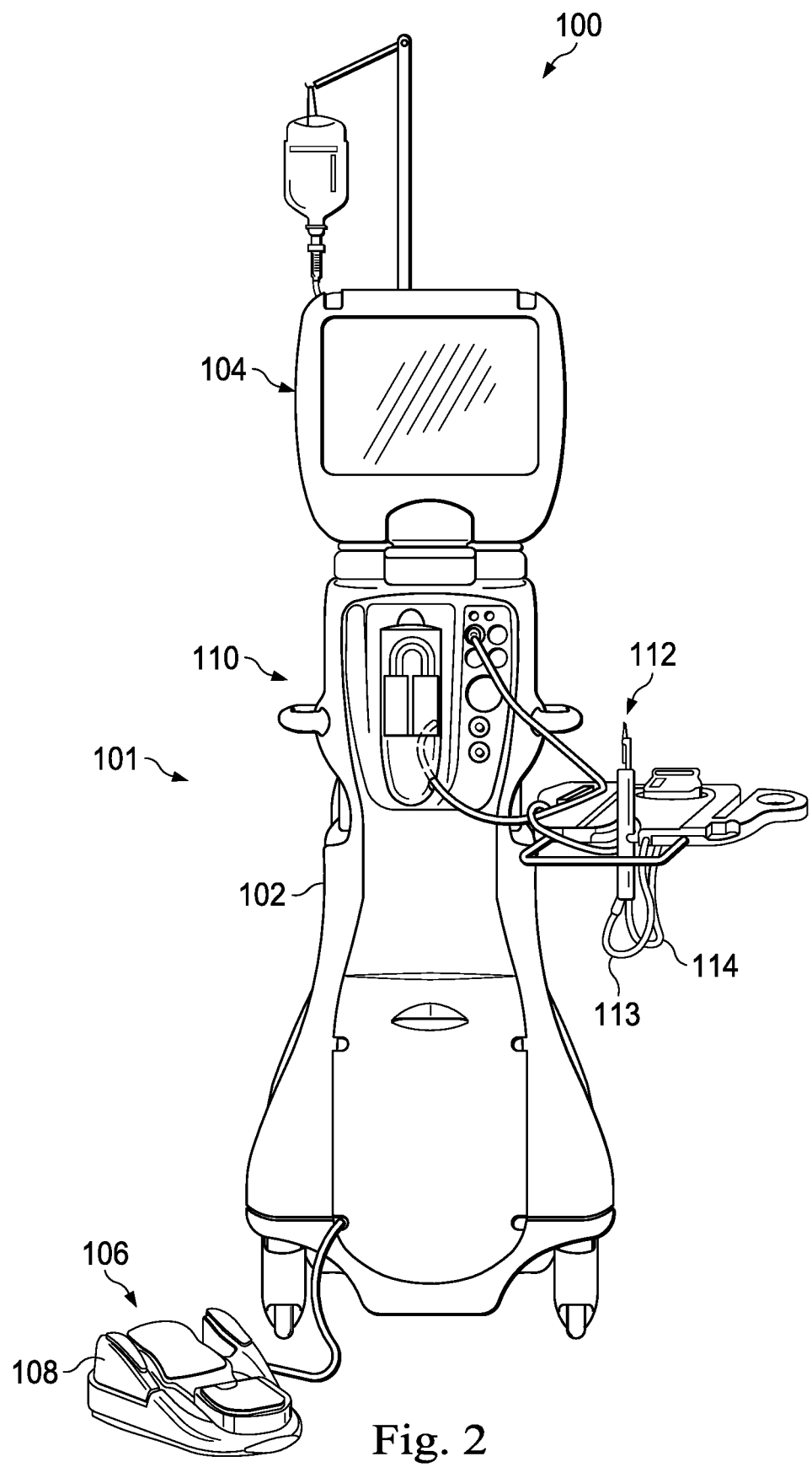
FIG. 2 is an illustration of an example ophthalmic surgical system.
Figure 3:
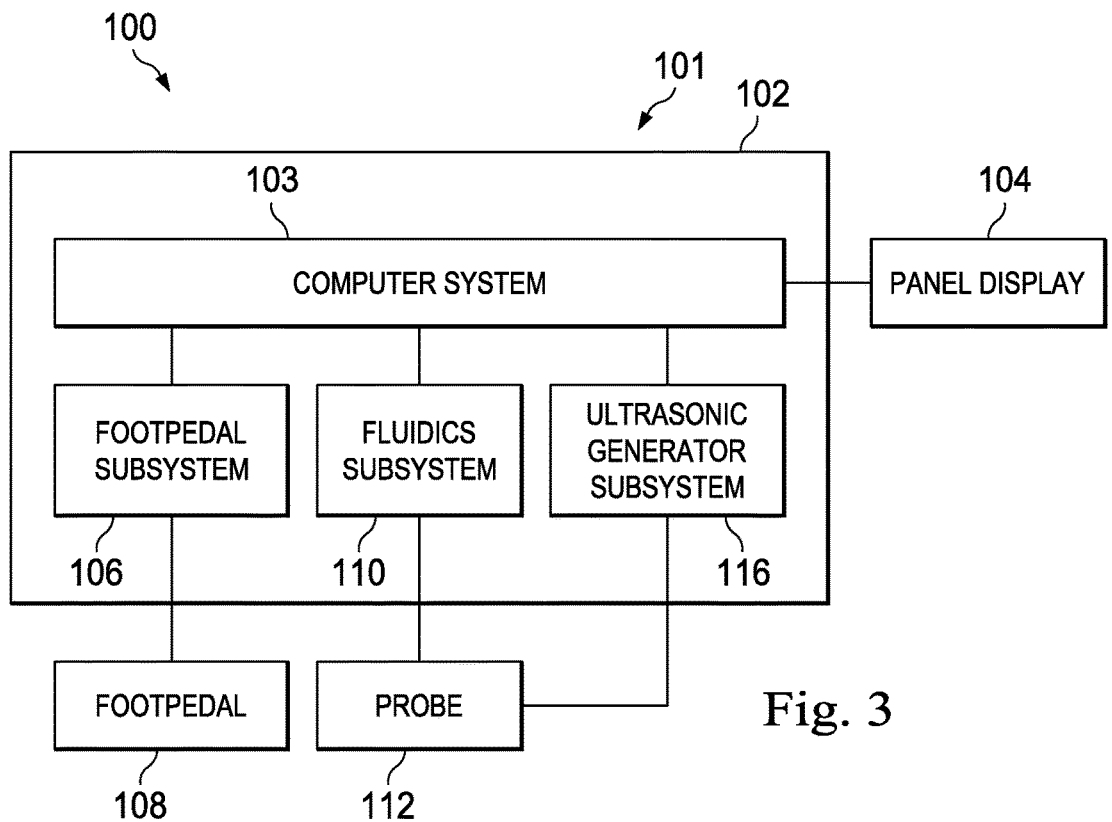
FIG. 3 is a block diagram of an example ophthalmic surgical system.

FIG. 2 illustrates an exemplary ophthalmic surgical system 100. FIG. 3 is a block diagram of the system 100 showing various subsystems that operate to perform an ophthalmic surgical procedure. Referring to FIGS. 2 and 3, the example system 100 includes a handheld probe 112 and a console 101. The console 101 includes a movable base housing 102 and an associated display screen 104 showing data relating to system operation and performance during a surgical procedure.

The system 100 includes at least a part of a plurality of subsystems. For example, the system 100 includes a foot pedal subsystem 106, a fluidics subsystem 110, and an ultrasonic generator subsystem 116, all of which cooperate with a computer system 103 to perform a phacoemulsification surgical procedure. The computer system 103 includes a processor and memory and may be disposed within the housing 102. The foot pedal subsystem 106 includes a foot pedal 108. The fluidics subsystem 110 includes a handheld probe, such as the handheld probe 112 having an integrated aspiration pump. The ultrasonic generator subsystem 116 provides an ultrasonic oscillation to a cutting needle of the handheld probe 112. In some implementations, some of subsystems 106, 110, 116 may include components or elements that are separable from and/or not disposed on the console 101. These subsystems may overlap and cooperate to perform various aspects of a surgical procedure.

One or more of subsystems 106, 110, and 116 may be in electrical communication with a computer system. In the illustrated example, the subsystems 106, 110, and 116 are in electrical communication with the computer system 103. In some implementations, the computer system 103 may transmit control signals to one or more of the subsystems 106, 110, and 116 to control operation of a probe associated therewith, such as, for example, the probe 112. The probe 112 and the console 101 may be connected by an electric cable 113 and one or more flexible conduits 114. The console 101 may transmit power to a driving mechanism that drives the integrated aspiration pump of a probe 112, such as probe 112, for example. The console 101 may also transmit power to a probe that supplies other driving mechanism(s). For example, the console 101 may provide electrical power to operate an ultrasonic cutting needle. In some implementations, the one or more flexible conduits 114 may supply irrigation fluid to the surgical site and carry aspiration fluid from the eye through the probe 112.

Figure 4:
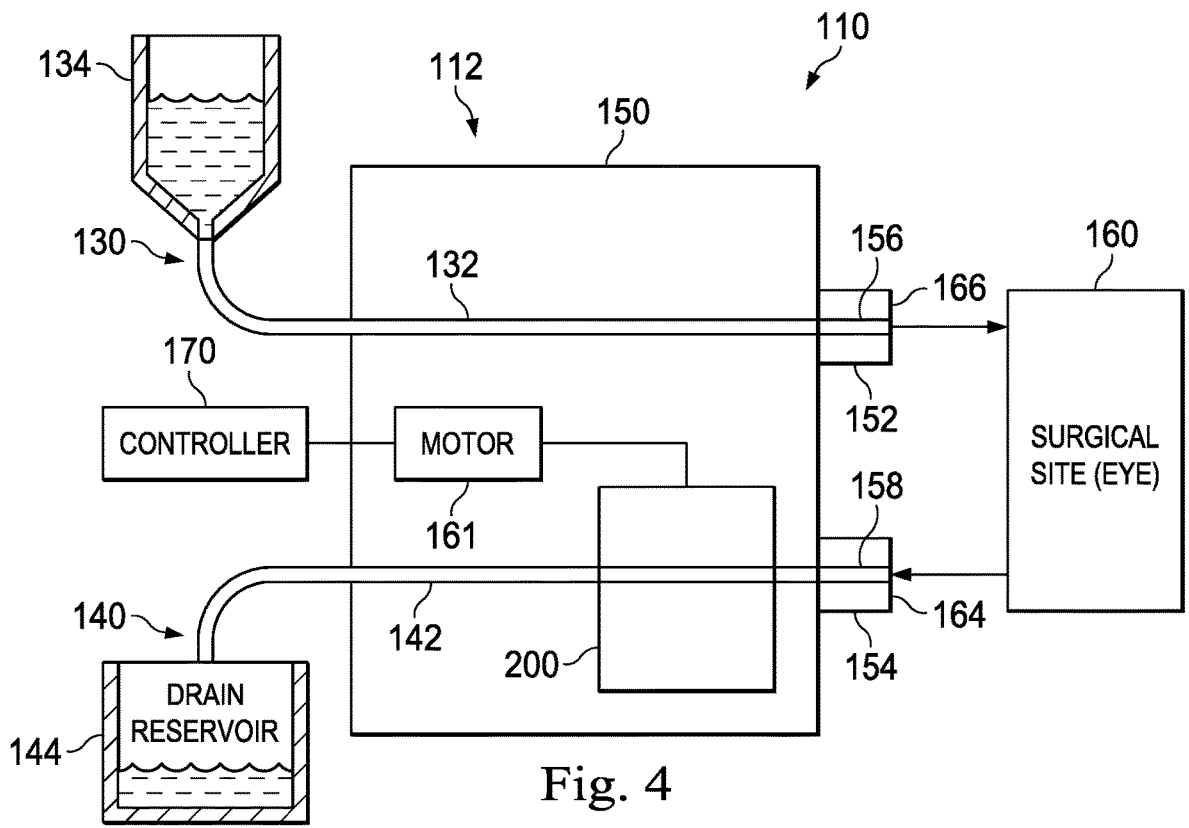
FIG. 4 is block diagram of the phacoemulsification probe.

FIG. 4 is a block diagram schematically illustrating a part of the fluidics subsystem 110 according to an exemplary implementation. The fluidics subsystem 110 includes an irrigation path 130, an aspiration path 140, and the probe 112. The probe 112 may include a housing 150 sized and shaped for grasping and handheld use by a user, such as a surgeon. In some implementations, the probe 112 may be a phacoemulsification probe that includes an irrigation sleeve 152 and a cutting needle 154. The irrigation sleeve 152 and the cutting needle 154 may extend from the housing 150. While the irrigation sleeve 152 and the cutting needle 154 are separately shown in FIG. 4 for ease of understanding, the irrigation sleeve 152 and the cutting needle 154 may be coaxial or otherwise arranged in different implementations. The irrigation sleeve 152 and the cutting needle 154 may be sized to penetrate and treat the eye 160 of the patient.

While the probe 112 may be characterized as a phacoemulsification probe in some implementations, it is understood that probe 112 may be a standalone aspiration probe. The probe 112 may also be another type of surgical probe having an integrated pump 200 and/or motor 161. For example, the probe 112 may be an illumination probe, a laser probe, and/or a vitreous cutting probe. In the example shown in FIG. 4, the probe 112 includes the integrated pump 200 and a motor 161. In other implementations, the probe 112 may include other types of drive mechanisms other than a motor. Further, in other implementations, the probe 112 may the integrated pump 200 or the motor 161 or both.

During the course of some phacoemulsification procedures, a tip 164 of the cutting needle 154 and an end 166 of the irrigation sleeve 152 may be inserted into the anterior segment of an eye 160 through a small incision in the outer tissue of the eye. To emulsify or otherwise break up a lens, the surgeon brings the tip 164 of the cutting needle 154 into contact with the lens of the eye 160, so that the vibrating tip 164 fragments the lens. Irrigation fluid may be delivered to the surgical site, e.g., into the anterior segment of the eye 160 from an irrigation fluid supply 134 via an irrigation lumen 156 of the sleeve 152. The resulting fragments are aspirated out of the eye 160 through an interior bore or lumen 158 of the cutting needle 154, along with irrigation solution provided to the eye during the procedure. The aspirated materials are delivered into a drain reservoir 144.

Throughout or during select periods of a procedure, irrigating fluid may be pumped into the eye 160. In some implementations, the cutting needle 154 may extend through the irrigation lumen 156 of the sleeve 152 defining an annular passage. The irrigating fluid may pass between the irrigation sleeve 152 and the cutting needle 154 in the annular passage and exit into the eye 160 at the end 166 of the irrigation sleeve 152 and/or from one or more ports or openings formed in the irrigation sleeve 152 near the end 166.

In the illustrated example, the probe 112 includes components of the irrigation path 130 including an irrigation conduit 132. In some instances, one or more components of the irrigation path 30 may be flexible and/or deformable tubing defining a lumen to convey the irrigation fluid. In the example shown in FIG. 4, the conduit 132 extends from the irrigation fluid supply 134 to the probe 112. At least a portion of the conduit 132 is disposed within the housing 150 and is in fluid communication with the irrigation fluid supply 134 and an irrigation lumen 156 of the sleeve 152. During a surgical procedure, irrigation fluid may flow from the irrigation fluid supply 134, through the irrigation conduit 132 and the irrigation lumen 156, and into the eye 160. The irrigation fluid may be a saline or balanced salt solution. The irrigation fluid may maintain intraocular pressure and may prevent collapse of the eye 160 during the surgical procedure by replacing fluid that is aspirated away from the eye 160. The irrigating fluid may also protect the eye tissue from the heat, such as heat generated by vibrations of the ultrasonic cutting needle 154. Furthermore, the irrigating fluid may suspend the fragments of the emulsified lens for aspiration from the eye 160. In some implementations, the irrigation fluid supply 134 may be spaced from the probe 112. For example, some implementations include the irrigation fluid supply 134 disposed on an intravenous pole at a fixed or adjustable height. Other implementations include the irrigation fluid supply 134 disposed within the console 101.

The probe 112 also may include components of the aspiration path 140. For example, the probe 112 may include all or part of an aspiration conduit 142. The aspiration conduit 142 may be in the form of a flexible and/or deformable tubing having a lumen to convey aspirated material. The conduits 132, 142 may be formed of any suitable resilient material, including silicone or other types of polymers.

As shown in FIG. 4, the conduit 142 extends from the probe 112 to the drain reservoir 144. At least a portion of the aspiration conduit 142 may be disposed within the housing 150. The aspiration conduit 142 is in fluid communication with an aspiration lumen 158 of the cutting needle 154 and the drain reservoir 144. Aspiration fluid flows from the eye 160 through the aspiration lumen 158 and the aspiration conduit 142 and collects in the drain reservoir 144. Aspiration fluid may include irrigation fluid (such as irrigation fluid that has been delivered to the eye 160 via the irrigation path), biological fluid from the eye 160, and/or biological matter from the eye 160, such as emulsified eye lens fragments. The drain reservoir 144 may be spaced from the probe 112, and may be disposed, for example, within the console 101 in some implementations.

The pump 200 may be associated with the aspiration path 140. The pump 200 may be arranged to interface with the aspiration conduit 142 to urge the aspiration fluid to flow away from the eye 160 and towards the drain reservoir 144. For example, the pump 200 may be a peristaltic pump driven by the motor 161. A motor shaft of the motor 161 may be mechanically coupled to a roller driver, such as a moving plate and/or moving cylinder, of the pump 200. Rotation of the motor shaft causes corresponding rotation of the roller driver. Various exemplary implementations of the motor 161 and/or pump 200, along with the motor shaft and the roller driver, are shown and/or described with respect to FIGS. 5-15.

In some implementations, the pump 200 or another pump may be arranged to interface with the irrigation conduit 132. For example, the pump 200 may be arranged to interface with the irrigation conduit 132 to urge the irrigation fluid to flow from the irrigation fluid supply 134 and towards the eye 160. Accordingly, the pump 200 may be implemented within the probe 112 to direct fluid from the eye 160 (along the aspiration conduit 142) and/or towards the eye 160 (along the irrigation conduit 132).

The fluidics subsystem 110 may also include a controller 170 in electrical communication with the motor 161. The controller 170 may include one or more processors and one or more memory devices. In some implementations, the processor may include one or more processing cores capable of performing parallel or sequential operations. In other implementations, the controller 170 may be a dedicated piece of hardware such as, for example and without limitation, an application specific integrated circuit (ASIC). The one or more memory devices may include any memory or module and may take the form of volatile or non-volatile memory including, without limitation, magnetic media, optical media, random access memory (RAM), read-only memory (ROM), removable media, or any other suitable local or remote memory component. The one or more memory devices may store one or more programs and/or data for use and/or execution by the one or more processors.

The motor 161 may operate in response to control signals transmitted by the controller 170. In some instances, the controller 170 may control the on/off status, operating frequency, and/or other parameters of the motor 161. For example, controller 170 may transmit a control signal to the motor 161 to increase and decrease the speed of the motor 161. Because the pump 200 is coupled to the motor 161, operation of the motor 161 in turn causes operation of the pump 200. The controller 170 may be distinct from the computer system 103 (FIG. 2) in some implementations. In other implementations, the controller 170 may be part of the computer system 103 and in communication with the motor 161.

Figure 5:
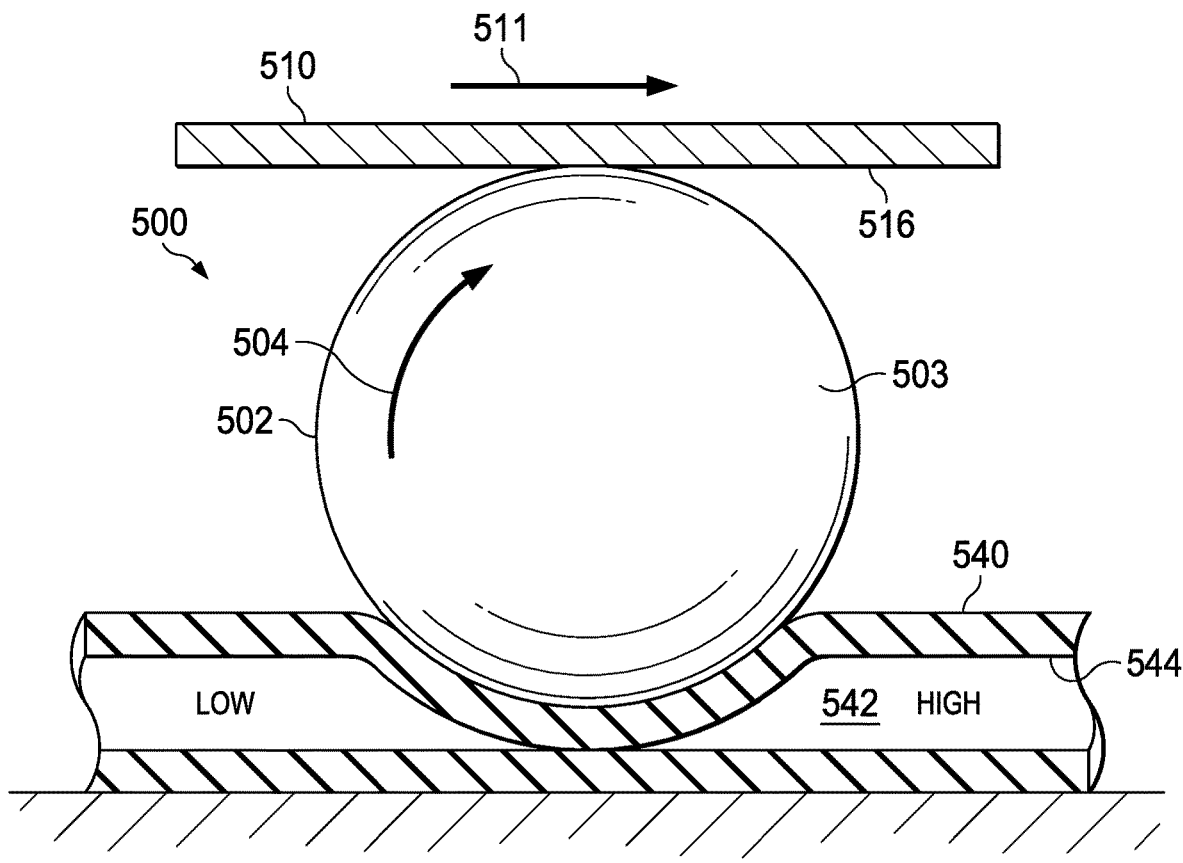
FIG. 5 is an illustration of a portion of an exemplary peristaltic pump.

FIG. 5 illustrates aspects of an exemplary peristaltic pump 500. The pump 500 may be or form a part of the pump 200 in FIG. 4. The conduit 540 may form a portion of the conduit 142 in FIG. 4.

The pump 500 includes a roller 502 and a roller driver 510. The roller 502 is moved along the conduit 540 by the roller driver 510. The conduit 540 defines a lumen 542. In the illustrated example, the roller driver 510 is a plate having a surface 516 in contact with the roller 502. In particular, the surface 516 of the roller driver 510 engages an outer peripheral surface 503 of the roller 502. In the illustrated example, the surface 516 of the roller driver 510 is generally planar. However, the surface 516 may be nonplanar. The roller 502 contacts and deforms the conduit 540. Particularly, as shown in FIG. 5, the roller 502 pinches the conduit 540 such that an inner surface 544 contacts itself to form a localized occlusion within the conduit 540. Fluid flow within the conduit 540 may be momentarily occluded at the point of contact with the roller 502. However, areas of high pressure and low pressure are created within the conduit 540 by contact with and movement of the roller 502. The created pressures within the conduit 540 causes fluid within the lumen 542 to flow in a direction 511. Thus, the pump 500 pumps material in a peristaltic manner.

The roller driver 510 may be coupled to a motor, such as, for example, the motor 161 shown in FIG. 3. Here, however, the roller 502 is directly driven by the motor 161. Rather, the roller 502 rotates in a direction 504 and translates in the direction 511 as a result of the roller driver 510 being driven in the direction 511. Thus, in contrast to the conventional pump 400 shown in FIG. 1, the roller 502 does not have and is not driven by an axle extending through a center of the roller 502. Instead, the roller driver 510, which is driven by the motor 161, contacts the outer peripheral surface 503 of the roller 502. Omitting the axle-roller interface in the pump 500 advantageously eliminates a friction source and minimizes the total amount of friction the motor 161 needs to overcome to operate the pump 500. Accordingly, the pump 161 included in the probe 112 to operate the pump 500 may be lighter, smaller, and less expensive.

The roller 502 may be any shape that provides suitable pumping action. In some implementations, the roller 502 is shaped as a spherical ball roller. In such implementations, the outer peripheral surface 503 of the roller 502 is an arc-shaped surface and is in contact with the surface 516 of the roller driver 510. In some implementations, the roller 502 may be formed from a metal, such as stainless steel. In other implementations, the roller 502 may be formed from a non-metallic material, such as silicone or other types of polymeric plastics and/or rubbers. For example, the roller 502 may be formed of a high durometer silicone.

Utilizing a spherical ball roller may advantageously simplify manufacturing of the pump 500. Previous peristaltic pumps required complex geometries for rollers and/or other components in contact with the elastic tubing. For example, previous peristaltic pumps utilized rollers with a tapered shape or a helical screw/scroll. Spherical ball rollers, which have simpler geometry, are easier to manufacture, obtain, and/or implement in the pump 500.

The peristaltic pump 500 of the probe 112 may include any number of rollers. For example, the pump 500 includes a single roller 502, illustrated in FIG. 5. In other instances, two or more rollers 502 may be used. For example, in some implementations, the pump 500 may use between two and 18 rollers. However, the scope is not so limited. Rather, any number of rollers 502 may be used in the pump 500. For example, an exemplary pump 800 shown in FIGS. 11 and 12 utilizes four rollers 802. Exemplary pumps 600, 700, and 900 shown in FIGS. 6, 7, and 13, respectively, include six rollers. An exemplary pump 750 shown in FIG. 10 includes twelve rollers 702 (four rollers 702 are shown and eight rollers 702 are hidden in the cross-sectional side view of FIG. 10).

Figure 6:
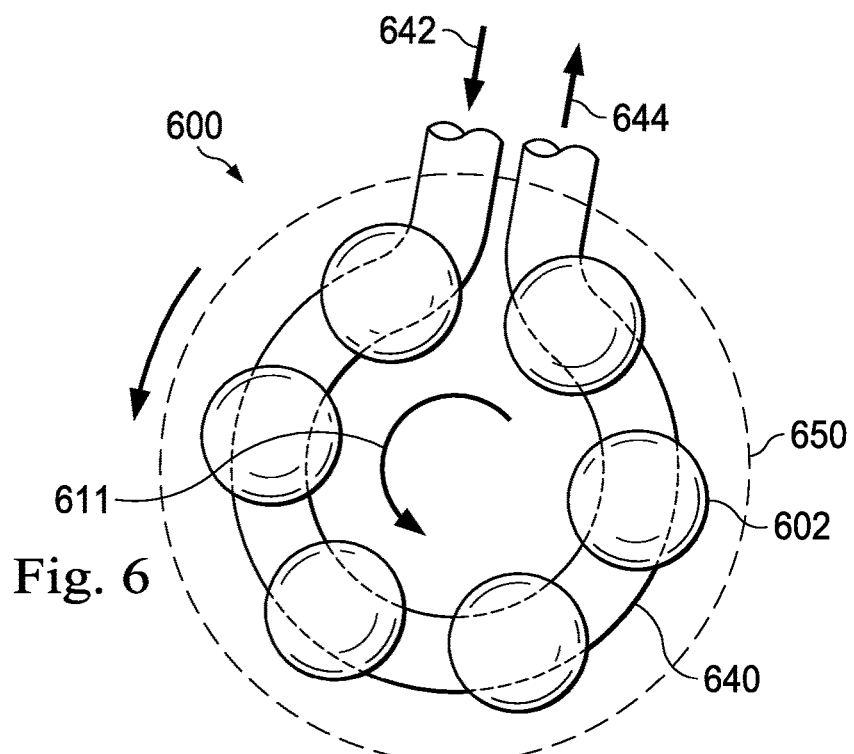
FIG. 6 is an illustration of exemplary aspects of a peristaltic pump.

Pumps within the scope of the disclosure may have the rollers arranged in a variety of configurations. For example, the rollers may be positioned relative to one another in any combination of longitudinal, axial/radial, and/or circumferential spacing. For example, as shown in FIGS. 6, 7, 12, and 13, respectively, the rollers 602 of the pump 600, the rollers 702 of the pump 700, the rollers 802 of the pump 800, and the rollers 902 of the pump 900 are arranged in a generally circular configuration. Further, the rollers may be spaced from one another around a circumference, as shown, for example, in FIG. 6. In some implementations, the rollers may be arranged such that there is at least one roller momentarily occluding fluid flow within the conduit to ensure that a pressure differential between high and low pressure regions in the conduit always exists. As shown in FIG. 6, the rollers are spaced from one another so that a portion of un-occluded tubing is located between two portions of tubing that are pinched, occluded, or otherwise deformed by adjacent rollers. The fluid within this un-occluded portion of the tubing is urged in the desired direction by the rollers.

In FIG. 5, the conduit 540 is illustrated as being disposed in a linear configuration. The roller driver 510 is moveable in a linear manner in the direction 511. Translation of the roller driver 510 causes corresponding linear displacement of the roller 502 along the conduit 540 in the direction 511. In other implementations, the conduit may be disposed in a non-linear configuration, and the roller driver and roller(s) may move along a non-linear path. For example, the roller driver and roller(s) may be arranged to move in one or more longitudinal, axial/radial, and/or circumferential directions. The roller driver and roller(s) may move along the same or different paths. Generally, the rollers(s) contact, deform, and move along the conduit. The roller driver is arranged to contact the roller(s) and facilitate movement of the roller along the conduit.

FIG. 6 illustrates a portion of a pump 600 having a plurality of rollers 602 arranged in a circular configuration over segment of a conduit 640. The segment of the conduit 640 shown in FIG. 6 is disposed in generally circular or ring-shaped manner. The circular configuration may advantageously allow for more compact packaging of the conduit 640 within a housing of a probe, such as the housing 150 of the example probe 112. In the example shown, the pump 600 rotates the rollers 602 in a counter-clockwise direction 611, thereby urging the fluid through the segment of the conduit 640 in the counter-clockwise direction 611. The pump 600 may also be operated in a clockwise direction. Boluses of material (e.g., fluid or a fluid mixture) may be carried by the conduit 640 in the volume between adjacent rollers 602. The fluid is pumped into the conduit 640 in a direction 642 and out of a conduit 640 in the direction 644.

The pump 600 includes a roller driver 650 that is in contact with the rollers 602. The roller driver 650 rotates in the counter-clockwise direction 611 such that the rollers 602 also rotate along the conduit 640 in the direction 611. The rollers 602 contact and deform the conduit 640 as the rollers 602 move along the conduit in the direction 611 to urge the fluid through the conduit 640.

Figure 7:
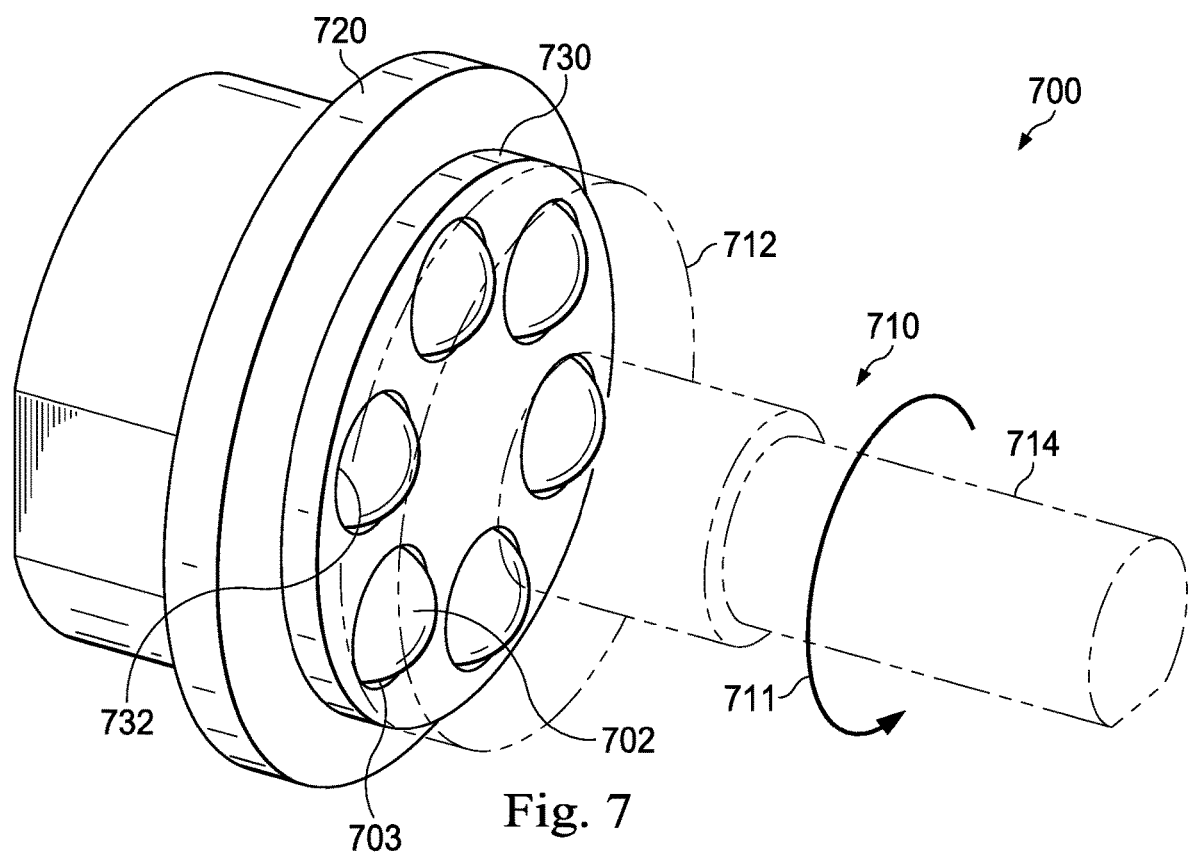
FIG. 7 is an illustration of exemplary peristaltic pump.
Figure 9:
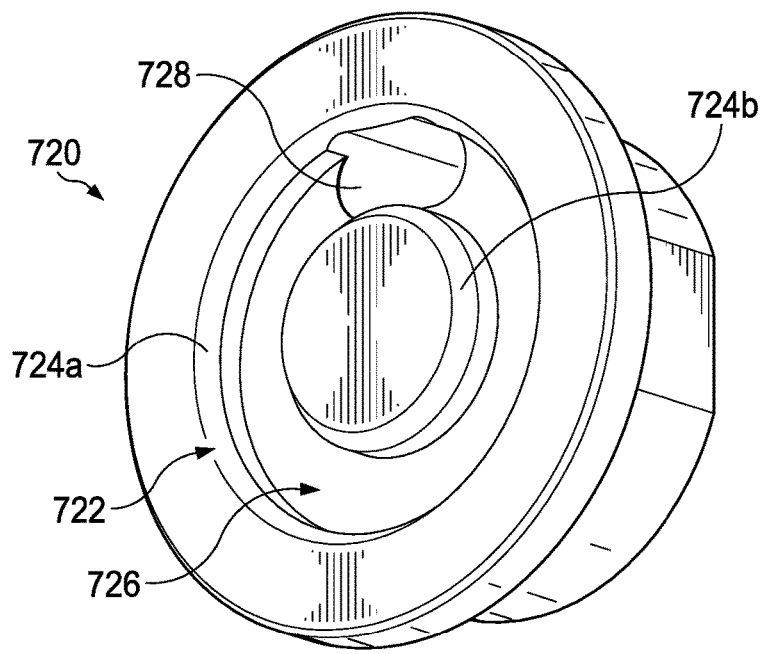
FIG. 9 is an illustration of a track housing of the peristaltic pump of FIGS. 7 and 8.
Figure 8:
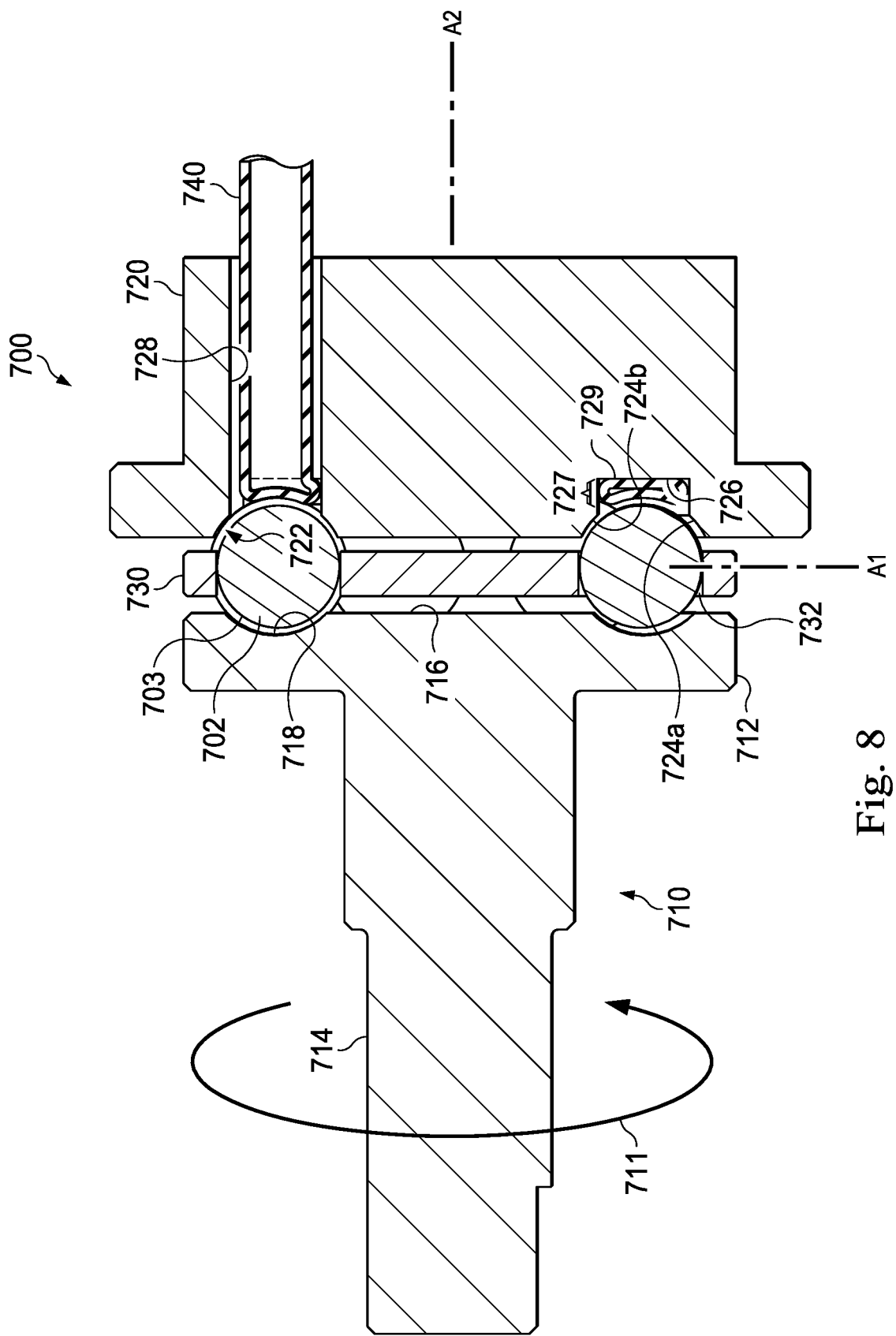
FIG. 8 is a cross-sectional side view illustration of the peristaltic pump of FIG. 7.

FIGS. 7-10 illustrate an example pump 700. The pump 700 includes rollers 702, a roller driver 710, a track housing 720, and a guide member 730. FIG. 7 is an illustration of the pump 700. FIG. 8 is a cross-sectional side view of the pump 700. FIG. 9 is an illustration of the track housing 720.

The pump 700 includes a plurality of rollers 702 arranged in a circular configuration. The roller driver 710 includes a plate 712 and a shaft 714. For example, the plate 712 and the shaft 714 may be integrally formed. In some implementations, the plate 712 may be in the form of a flange formed on the shaft 714, such as on an end of the shaft 714. The motor 161 may be mechanically coupled to the shaft 714 to rotate the shaft 714 in a direction 711. The plate 712 includes a surface 716, shown in FIG. 8, that contacts the outer peripheral surfaces 703 of the rollers 702 to frictionally drive the rollers 702. The outer peripheral surfaces 703 of the rollers 702 and the surface 716 of the plate 712 engage one another such that rotation of the plate 712 correspondingly rotates the rollers 702, causing each of the rollers 702 to rotate about an individual axis A1, each of the axes A1 extending radially outward from and perpendicular to longitudinal axis A2. Collectively, the rollers 702 rotate along a circumferential path about the longitudinal axis A2 of the roller driver 710. The surface 716 of the plate 712 includes an annular groove 718 sized and shaped to receive or accommodate respective portions of the rollers 702. In some implementations, the surface 716 may omit the annular groove 718 but, rather, include a plurality of individual indentations. Each of the indentations receives one of the rollers 702 and has a shape that corresponds to the outer peripheral surface 703 of the rollers 702. In other implementations, the surface 716 may be generally planar and exclude the annular groove or individual indentations.

As shown in FIG. 9, the track housing 720 forms a circular channel 726. The channel 726 defines a track 722 that forms a path for movement of the rollers 702. The track 722 includes edges 724a and 724b. In the example shown, the edges 724a and 724b are defined by chamfers formed in outer an inner edges, respectively, of the channel 726. The rollers 702 travel along the channel 726 between the edges 724a and 724b while portions of the rollers 702 are in contact with the edges 724a and 724b. In some implementations, a width of the track 722 may be less than a diameter of the rollers 702.

The channel 726 includes an annular gap 727 formed between the track 722 and an end surface 729. A flexible conduit 740 is positioned within the annular gap 727 formed in the channel 726. In some instances, a depth of the gap 727 is selected such that, the conduit 740 is fully occluded by the rollers 702 as the rollers 702 are moved along the track 722. In other implementations, the depth of the gap 727 may be such that the conduit 740 is prevented from being fully occluded by the rollers 702 as the rollers 702 are moved along the track 722. The track 722 and the channel 726 are arranged such that the rollers 702 rotate around the track 722 while contacting and deforming the flexible conduit 740.

The rollers 702 abut and roll along the edges 724a and 724b while rotating around the track 722 and along the conduit 740. Contact between the rollers 702 and the edges 724a and 724b prevent the roller from deforming of the conduit 740 beyond a selected amount by limiting longitudinal ingress of the rollers 702 into the channel 726. This advantageously prevents undesirably high loads on the conduit 740, thereby decreasing wear on the conduit 740 and preventing tearing of the conduit 740. The track housing 720 also includes a port 728 through which the conduit 740 extends, as shown, for example, in FIG. 8. In some instances, both ends of the conduit 740 extend through the port 728. In other implementations, the track housing 720 may include separate ports through which opposing ends of the conduit 740 extend.

In FIG. 8, the conduit 740 is illustrated as being a distinct length of tubing. However, the scope of the disclosure is not so limited. In other implementations, the conduit 740 may be otherwise formed. For example, the conduit 740 may be integrated or integrally formed in the track housing 720. In some implementations, a resilient material may be overmolded onto the track housing 720 and positioned around the track 722, such that the overmolded resilient material forms a seal around the track 722. In some implementations, the overmolded resilient material forming the conduit 740 may have a convex cross-sectional shape. In some implementations, the resilient material and a surface of the channel 726 define a lumen through which fluid may be conveyed. Fluid may freely flow within the lumen (e.g., without distinct tubing). The pump 700 may urge the fluid to flow by compressing the resilient material with the rollers 702 as the rollers 702 move along the track 722. An integrally formed conduit may advantageously make manufacturing more efficient and reduce manufacturing costs. The conduit may be formed within the track housing 720 at the same time as the track housing 720 is manufactured. As a result, an additional step of positioning the distinct tubing within the channel 726 may be avoided.

As shown in FIGS. 7 and 8, the pump 700 includes a guide member 730 disposed between the roller driver 710 and the track housing 720. The guide member 730 includes a plurality of openings 732 extending longitudinally through the guide member 730. The openings 732 are sized to receive respective rollers 702. The rollers 702 are positioned within the openings 732 such that portions of the rollers 702 protrude from both longitudinal sides of the guide member 730.

The guide member 730 is oriented so that a reference plane extending through the centers of all of the rollers 702 contains or is parallel with the axes A1 and is orthogonal to the longitudinal axis A2. The guide member 730 may be arranged to maintain the circumferential spacing, radial positioning, and/or axial positioning of the rollers 702 as the rollers 702 are rotated along the conduit 740 by the plate 712. In that regard, the guide member 730 may preserve the circular configuration of the rollers 702 by preventing undesired circumferential movement of the rollers 702 relative to one another, radial movement, and/or axial movement of the rollers 702. This may advantageously ensure regular, periodic, peristaltic fluid flow within the conduit 740 by keeping the rollers 702 at known, fixed locations relative to one another even as the rollers 702 are driven along the conduit 740 by the roller driver 710.

Figure 10:
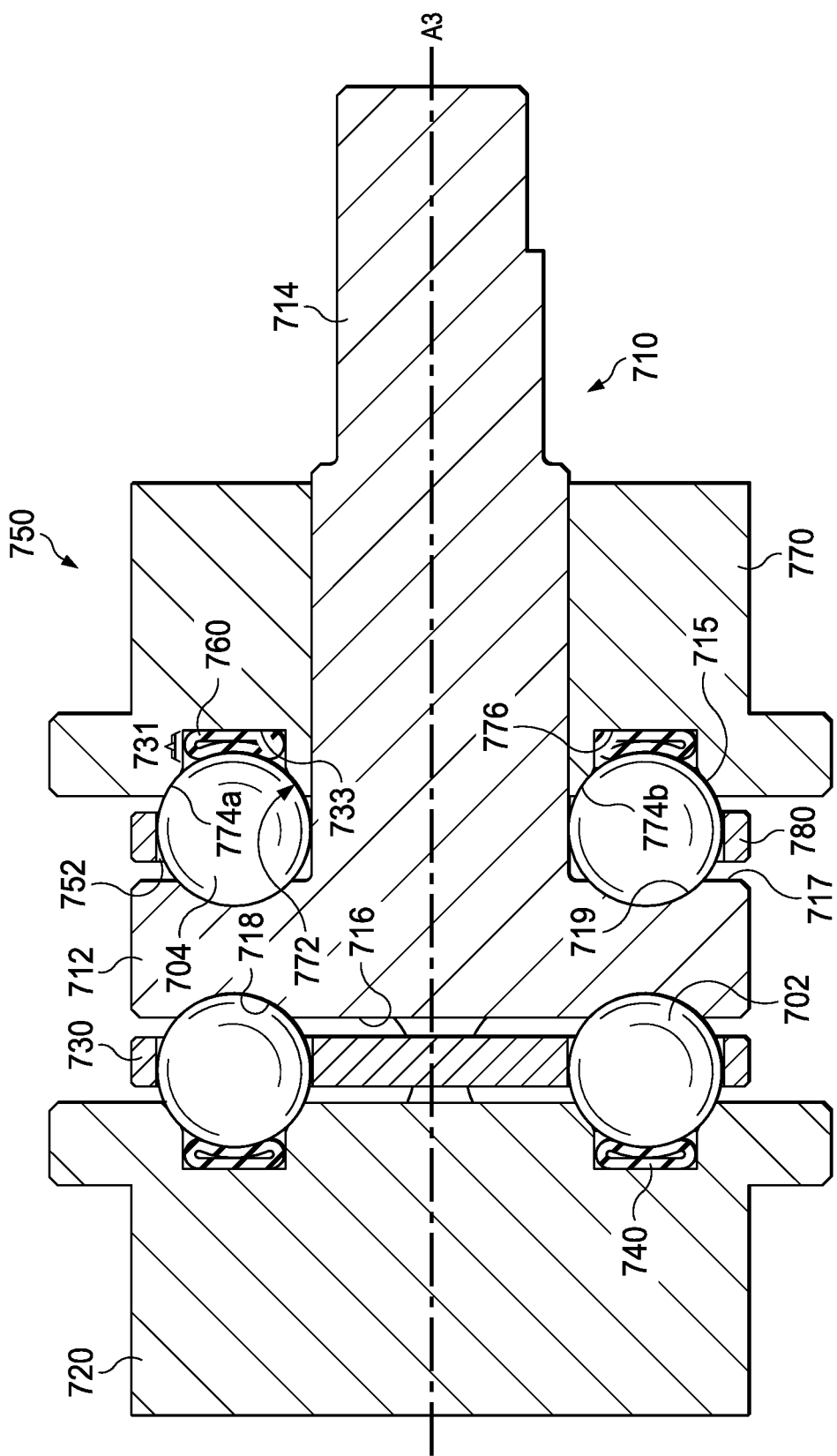
FIG. 10 is cross-sectional side view illustration of an exemplary peristaltic pump.

FIG. 10 is a cross-sectional side view of another exemplary pump 750 according to another implementation. The pump 750 includes a plurality of rollers 702, a roller driver 710, a track housing 720, and a guide member 730. The rollers 702, the track housing 720, the guide member 730, and the roller driver 710 may be similar to those described above in the context of the pump 700. However, the roller driver 710 also includes a surface 717 formed on plate 712 that contacts outer peripheral surfaces of a plurality of rollers 704, as explained below. The pump 750 additionally includes the plurality of rollers 704 positioned within a support member 780 and a channel 776 formed in a track housing 770. A track 772 is defined by and edges 774a and 774b of the channel 776. Similar to the track 722, described above, the edges 774a and 774b are defined by chamfers formed in outer an inner edges, respectively, of the channel 776. The rollers 704 are conveyed along the track 722 by rotation of the roller driver 710. A conduit 760 is positioned within the channel 776. As the rollers 704 are moved along the track 722 to compress the conduit 760, the rollers 704 are in contact with the edges 774a and 774b. The rollers 704 contact and deform the conduit 760 so as to occlude all or part of a lumen formed within the conduit 760. The edges 774a and 774b of the track 772 limit an amount the rollers are permitted to extend into the channel 776 and an amount of by which the conduit 760 is occluded by the rollers 704.

Also similar to the conduit 740, the conduit 760 may be integrated or integrally formed in the track housing 770. In some implementations, a resilient material may be overmolded onto the track housing 770 and positioned around the track 772, such that the overmolded resilient material forms a seal around the track 772. In some implementations, the overmolded resilient material forming the conduit 760 may have a convex cross-sectional shaped. In some implementations, the resilient material and a surface of the channel 776 define a lumen through which fluid may be conveyed, in some instances, and define a lumen for fluid flow including the channel 776.

The channel 776 includes an annular gap 731 formed between the track 722 and an end surface 733. The flexible conduit 760 is positioned within the annular gap 731 formed in the channel 776. In some instances, a depth of the gap 731 is selected such that, the conduit 760 is fully occluded by the rollers 704 as the rollers 704 are moved along the track 772. In other implementations, the depth of the gap 731 may be such that the conduit 760 is prevented from being fully occluded by the rollers 704 as the rollers 704 are moved along the track 772. The track 772 and the channel 776 are arranged such that the rollers 704 rotate around the track 772 while contacting and deforming the flexible conduit 760.

The rollers 704 are positioned within recesses 752 formed in the support member 780. The support member 780 operates similarly to the guide member 370 in that the support member 780 maintains a circumferential spacing, radial positioning, and/or axial positioning of the rollers 704 as the rollers 704 are rotated along the conduit 760 by the plate 712. As shown in FIG. 10, the surface 717 includes an annular groove 719 sized and shaped to receive or accommodate respective portions of the rollers 704. In other implementations, the surface 717 may omit the annular groove 719.

In operation, the roller driver 710 is rotated about axis A3 relative to both the track housing 720 and the track housing 770. The surface 717 of the plate 712 contacts the outer peripheral surfaces 715 of the rollers 704, and the surface 716 contacts the outer peripheral surfaces 703 of the rollers 702. The surface 717 of the plate 712 frictionally engages the outer peripheral surfaces 715 of the rollers 704 to rotate the rollers 704. In a similar manner, the rollers 702 are also rotated by the surface 716. The surfaces 716 and 717 are on opposite sides of the plate 712. The plate 712 simultaneously drives the different sets of rollers 702 and 704 to urge fluid through conduits 740 and 760, respectively, when the roller driver 710 is rotated about axis A3. In some implementations, the conduits 740 and 760 may be in fluid communication with one another. Accordingly, the conduits 740 and 760 may be different segments of the same fluid pathway. In other implementations, the conduits 740 and 760 may be may be separate from each other and, thus, not in fluid communication with each other. In some implementations, the track housing 770 may have one or more ports formed therein (which may be similar to port 728, described above), through which the conduit 760 may pass.

Figure 11:
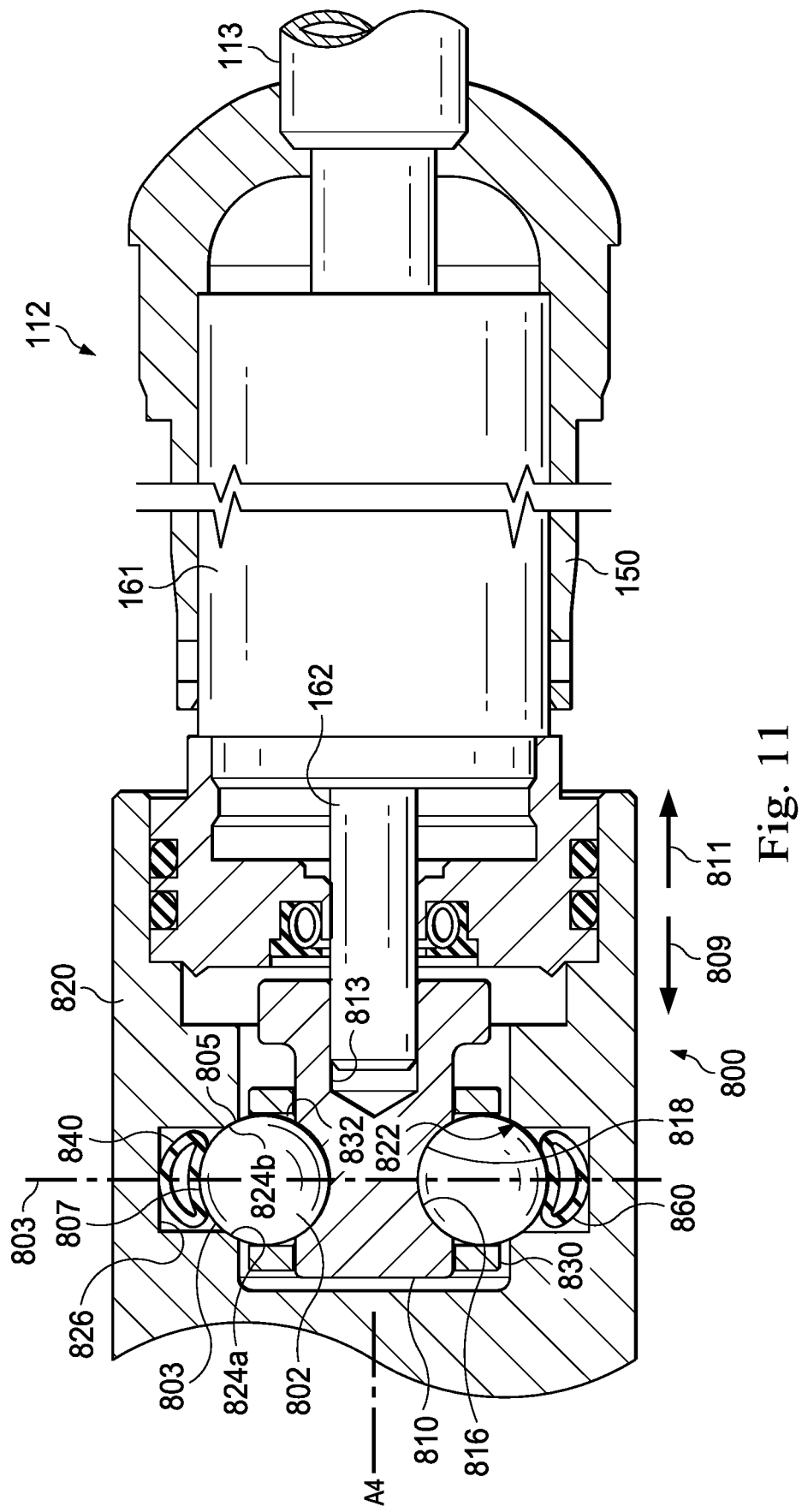
FIG. 11 is cross-sectional side view illustration of a portion of a handheld probe including an exemplary peristaltic pump.
Figure 12:
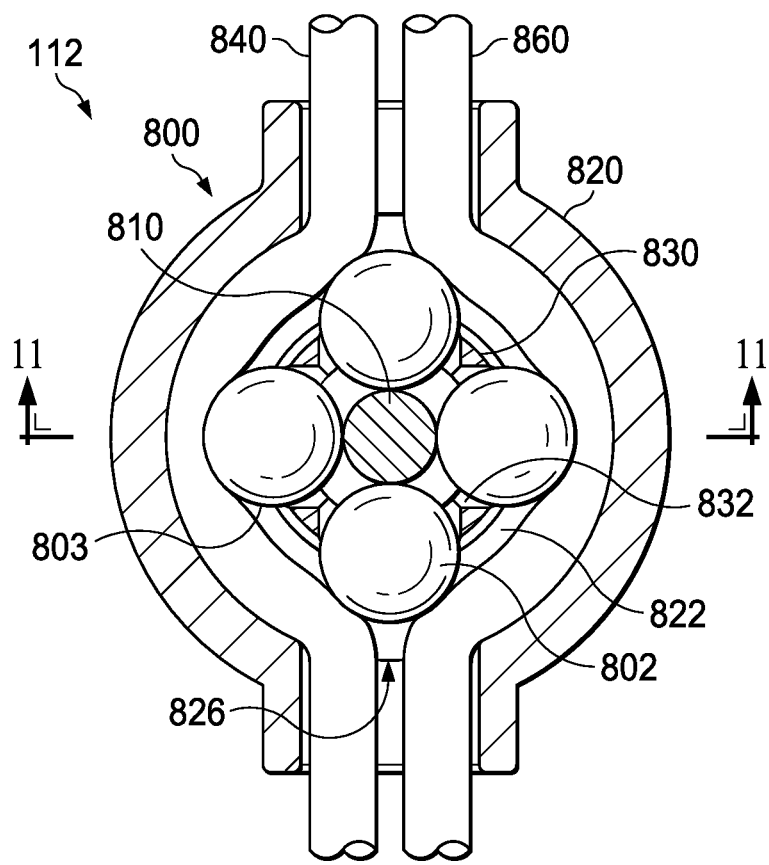
FIG. 12 is cross-sectional end view illustration of the handheld probe and the peristaltic pump of FIG. 11.

FIGS. 11 and 12 illustrate a portion of a probe 112. The probe 112 includes a motor 161 and an exemplary peristaltic pump 800 having rollers 802 and a roller driver 810. FIG. 11 is a cross-sectional side view of the probe 112 taken along section line 11-11 in FIG. 12. FIG. 12 is a cross-sectional end view of the probe 112.

The pump 800 and the motor 161 are disposed within a housing 150 of the probe 112. An electrical cable 113 provides power to the motor 161. The motor 161 includes a motor shaft 162. The motor shaft 162 is coupled to a roller driver 810 of the pump 800 such that the roller driver 810 is rotated when the motor shaft 162 is rotated. In some implementations, the roller driver 810 is attached to the motor shaft 162. In the illustrated implementation, the roller driver 810 is a rotating cylinder. The motor shaft 162 is received within a bore 813 of the roller driver 810. Rotation of the shaft 162 causes corresponding rotation of the roller driver 810.

The roller driver 810 has a generally cylindrical shape. A surface 816 of the roller driver 810 is in contact with outer peripheral surfaces 803 of one or more rollers 802. The surface 816 of the roller driver 810 may include a groove 818 in which the rollers 802 are positioned. The groove 818 is sized and shaped to accommodate at least one of the rollers 802. In the illustrated example, the groove 818 is sized and shaped to receive all of the rollers 802. In some implementations, the roller driver 810 is situated orthogonally to a reference plane 803 that includes the centers of all of the rollers 802. The reference plane 803 divides each of the rollers 802 into a first half 805 and a second half 807. At least a portion of the groove 818 extends around a portion of the first half 805, a portion of the second half 807, or a portion of both the first half 805 and the second half 807. In some implementations, at least a distal portion of the roller driver 810 extends longitudinally beyond the rollers 802 in a first direction 809, a second direction 811, or in both the first and second directions 809 and 811.

The pump 800 includes a track housing 820. A channel 826 is formed in the track housing and defines a track 822. During operation of the pump 800, the rollers 802 are moved along the track 822. A conduit 840 and a conduit 860 are disposed in a portion of the channel 826. The track 822 defines a circular path, and the conduits 840 and 860 are compressed by the rollers 802 as the rollers 802 are moved along the track 822. The track 822 is defined by chamfered edges 824a and 824b of the channel 826.

As shown in FIG. 12, each of the conduits 840 and 860 is positioned within a respective portion of the channel 826 in a generally semicircular configuration. While two conduits 840 and 860 are shown, it is understood that pump 800 may be utilized with one conduit or more than two conduits in some instances. In some implementations, one conduit can be positioned within the channel 826 in a generally circular configuration, such as shown, for example, in FIG. 6. The edges 824a and 824b limit radial movement of the rollers 802 into the channel 826 and prevent damaging deformation of the conduits 840 and 860 by the rollers 802.

In operation, the roller driver 810 drives the rollers 802 in contact with the edges 824a and 824b along the circular path defined by the track 822 about a longitudinal axis A4 of the housing 150. The rollers 802 are periodically in contact and occlude the conduits 840 and 860 to drive material respectively therethrough. Various portions of the conduits 840 and 860 come into contact with the rollers 802 as the rollers 802 move in response to motion of the roller driver 810.

Although FIG. 11 shows lumens 841 and 861 of the conduits 840 and 860, respectively, only partially occluded as the rollers 802 ride over and compress the conduits 840 and 860, the scope of the disclosure is not so limited. In some implementations, the rollers 802 may only partially compress the conduits 840 and 860 such that the lumens 841 and 861 is only partially restricted. However, in other implementations, the rollers 802 may fully compress the conduits 840 and 860 such that the lumens and fully occlude the lumens 841 and 861. In still other implementations, the conduits 840 and 860 and/or a size of the channel 826 or track 822 may be selected such that one of the lumens 841 and 861 is fully occluded while the other of the lumens 841 and 861 is only partially occluded.

A support member 830 is positioned between the roller driver 810 and the track housing 820. A plurality of recesses 832 are formed in the support member 830 are sized and shaped to receive the rollers 802. The support member 830 restricts longitudinal movement of the rollers 802 (i.e., movement of the rollers 802 in the first and second directions 809 and 811) as the roller driver 810 drives rollers 802 to rotate about the longitudinal axis A4.

Figure 13:
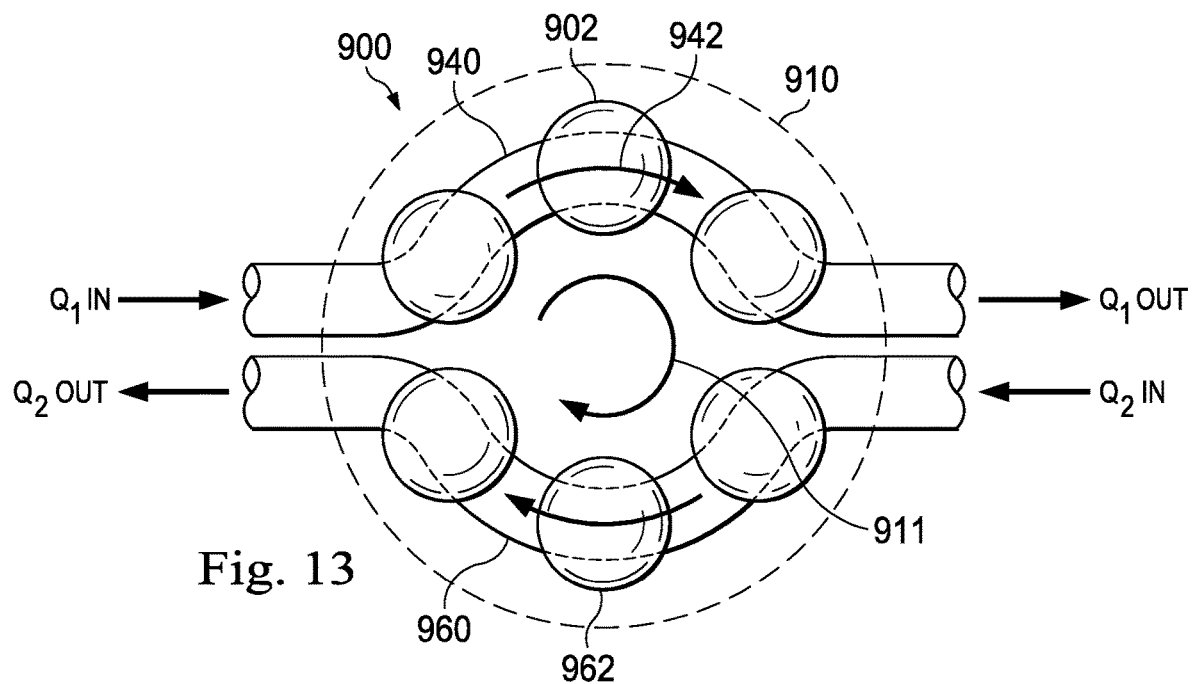
FIG. 13 is an illustration of exemplary aspects of a peristaltic pump.

FIG. 13 illustrates an exemplary peristaltic pump 900. Rollers 902 are arranged in a circular configuration. A roller driver 910 drives the rollers 902 to rotate in a circular path in a direction 911. The rollers 902 contact conduits 940 and 960 causing material contained within the conduits 940 and 960 to be conveyed in a manner as described above. The rollers 902 may fully or partially occlude lumens formed in the conduits 940 and 960. The pump 900 is arranged to pump fluid in the conduits 940 and 960 in different directions. For example, the rollers 902 urge the material (e.g., a fluid) in the conduit 940 in the direction 942 and the material (e.g., a fluid) in the conduits 960 in the direction 964. $Q_1$ IN and $Q_1$ OUT represent a flow rate of material into and out of the pump 900, respectively, via the conduit 940. $Q_2$ IN and $Q_2$ OUT represent a flow rate of material into and out of the pump 900, respectively, via the conduit 960. The direction 964 is different than the direction 962. Particularly, in the illustrated example, the direction 964 is opposite the direction 962. Accordingly, movement of the rollers 902 in a single direction 911 can urge material in two different directions. In some implementations, the conduits 940 and 960 may form parts of separate pathways that do not fluidly communicate with each other. In other implementations, the conduits 940 and 960 may be different segments of the same fluid pathway. Thus, while the material in the conduits 940 and 960 may flow in different directions 942 and 962, the material in both conduits 940 and 960 may be material being pumped away from the eye 160 via an aspiration conduit, such as the aspiration conduit 142 shown in FIG. 3.

Figure 14:
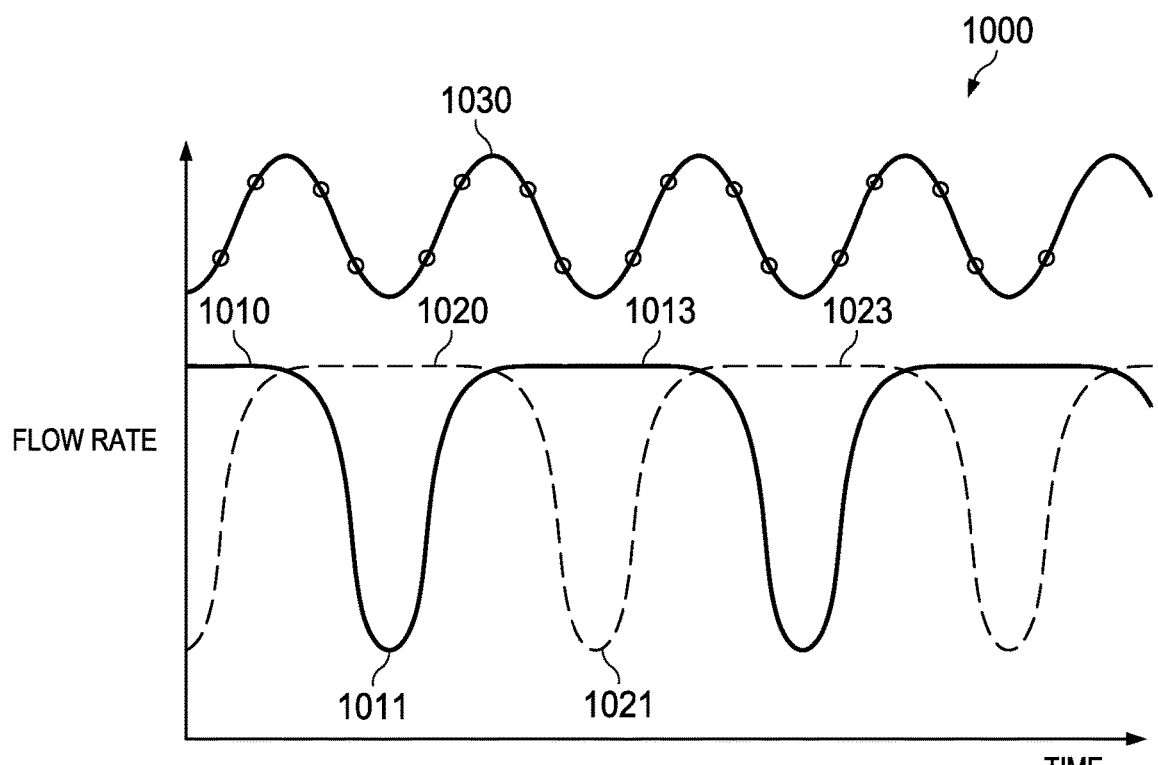
FIG. 14 is a graph illustrating exemplary aspects of the peristaltic pump of FIG. 13.

FIG. 14 shows a graph 1000 that illustrates how the arrangement of FIG. 13 may advantageously minimize pulsations in the output of the pump 900. The benefits associated with graph 1000 are applicable to the other pumps described herein. Pulsations describe periodic increases and decreases in the fluid output of the pump 900 which occur because of the configurations of the conduits 940 and 960 and/or the rollers 902. Curve 1010 illustrates the flow rate within the conduit 940 alone, and curve 1020 illustrates the flow rate within the conduit 960 alone. The curves 1010 and 1020 include minimas 1011 and 1021, respectively. The minima 1011 and 1021 represent a portion of the conduits 940 and 960, respectively, that are occluded as a result of contact with the rollers 902. The minima 1011 and 1021 reflect a reduced flow rate through the conduits 940 and 960, respectively. The curves 1010 and 1020 also include maxima 1013 and 1023. Where the rollers 902 fully occlude the conduits 940 and 960, these portions of the conduits 940 and 960 contain essentially no material. The maxima 1013 and 1023 represent a portion of the conduits 940 and 960, respectively, that are disposed between rollers 902. These portions of the conduits 940 and 960 contain a volume of material defined by a portion of the respective lumens formed in the conduits 940 and 960 between the rollers 902. The conduits 940 and 960 periodically output the boluses of fluid carried within the volume in the conduits 940 and 960 between adjacent rollers 902. The relatively large variations in the flow rates (the difference between the maxima and minima) illustrated by curves 1010 and 1020 may be indicative of this periodic output of fluid when considering the each of the conduits 940 and 960 independent of the other.

The arrangement of pump 900 advantageously minimizes flow rate variations by configuring the conduits 940 and 960 and the rollers 902 so that the flow within conduits 940 and 960 is 180° out of phase of each other. Thus, the maxima and minima of the flow rates illustrated in the curves 1010 and 1020 cancel one another. With such a configuration, as illustrated by the curve 1030, variations in the net or combined flow rate (the difference between the maxima and minima) through the conduits 940 and 960 are reduced, making for a more continuous flow with lower minima as compared to the flow rates through the individual conduits 940 and 960. Accordingly, the pump 900 advantageously has a smoother (i.e., less fluctuation) and more continuous total fluid output. While two conduits 940 and 960 are illustrated in FIG. 13, it is understood that three or more conduit segments may be implemented in the pump 900 to further reduce fluctuation of the fluid flow to an even greater extent.

Figure 15:
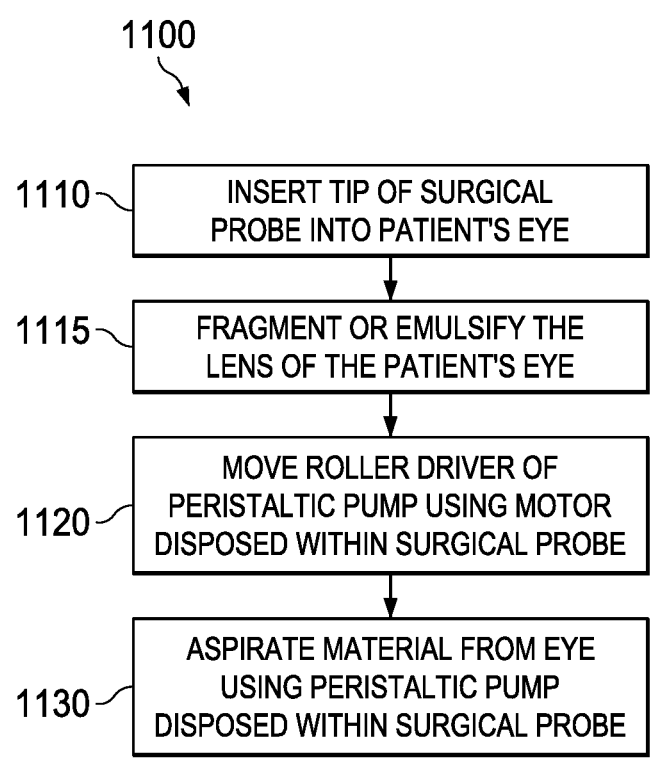
FIG. 15 is a flow diagram of an example ophthalmic surgical method.

FIG. 15 is a flow diagram of an example ophthalmic surgical method 1100. It is understood that the steps of method 1100 may be performed in a different order than shown in FIG. 15, additional steps may be provided before, during, and/or after the described steps, and/or some of the steps described may be replaced or eliminated in other implementations. One or more of steps of the method 1100 may be carried out by a medical professional, such as a surgeon, during an ophthalmic surgical procedure.

At 1110, the method 1100 includes inserting a tip of a surgical probe into a patient's eye. For example, a surgeon may insert a tip of a cutting needle into the anterior portion of the eye 160. For example, the tip 164 of the cutting needle 154 of the probe 112, as shown in FIG. 2, may be inserted into a patient's eye. The cutting needle may include an aspiration lumen 158, such as, for example, the aspiration lumen 158 formed in the cutting needle 154. At 1115, the surgeon contacts the tip with the lens of the eye. The tip is vibrated at a high rate (e.g., ultrasonically), causing the lens to become fragmented or emulsified. The probe also may include an irrigation sleeve, such as, for example, irrigation sleeve 152. The irrigation sleeve includes an irrigation lumen, e.g., irrigation lumen 156, through which irrigation fluid is delivered to the eye.

The method 1100 also includes aspirating fluid from the eye using a peristaltic pump disposed within the surgical probe, such as using any of the peristaltic pumps described herein. At 1120, the pump may interface with an aspiration conduit, such as, for example, the aspiration conduit 142. The aspiration conduit may be flexible or deformable tubing, for example. The aspiration conduit may be placed in fluid communication with an aspiration lumen formed in the cutting needle, such as aspiration lumen 158 formed in the cutting needle 154. The pump may include one or more rollers in contact with the aspiration conduit. The roller(s) are placed in contact with the aspiration conduit, and, as the rollers are driven by a roller driver, as explained above, the roller(s) occlude a lumen formed within the aspiration conduit to pump material peristaltically. The roller driver may be a rotating plate or a rotating cylinder, as explained above, and is arranged to translate, rotate, and/or otherwise move the roller(s). The aspiration conduit to pump fluid away from the eye.

Operation of the pump to cause the roller(s) to move along and compress the aspiration conduit in a manner described herein results in pumping and removal of aspiration fluid from the eye, as indicated at 1130. The aspiration fluid may include the irrigation fluid and/or biological material, such as the fragmented/emulsified lens particles.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic surgical system comprising:
   a handheld probe comprising:
   a housing sized and shaped for grasping by a user;
   a tip extending from the housing and being sized to penetrate and treat an eye of a patient, the tip including an aspiration lumen arranged to carry material away from the eye; and
   a peristaltic pump disposed within the housing, the peristaltic pump comprising:
   a deformable conduit comprising a conduit lumen extending therethrough, the conduit lumen in fluid communication with the aspiration lumen;
   a roller in contact with the deformable conduit and comprising an outer peripheral surface forming a majority of an outer surface area of the roller, the roller engaged with the deformable conduit to cause the deformable conduit to deform; and
   a roller driver in contact with the outer peripheral surface of the roller, the roller movable along the deformable conduit in response to movement of the roller driver to cause movement of the material within the conduit lumen therealong;

wherein the peristaltic pump comprises a plurality of rollers arranged in a circular configuration, and wherein the plurality of rollers are in contact with the deformable conduit and disposed between the deformable conduit and the roller driver;

wherein the roller driver comprises a groove sized and shaped to accommodate the plurality of rollers.

2. The system of claim 1, wherein the roller driver does not include an axle extending through the roller.

3. The system of claim 1, wherein the roller driver comprises a surface in contact with the plurality of rollers.

4. The system of claim 1, wherein the peristaltic pump further comprises a track housing defining a channel, wherein the channel defines a track along which the plurality of rollers travels.

5. The system of claim 4, wherein the deformable conduit is positioned within the channel, and wherein the plurality of rollers are arranged to move along the track while in contact with the deformable conduit and the roller driver.

6. The system of claim 5, wherein the track comprises a contact surface that limits deformation of the deformable conduit by limiting movement of the plurality of rollers into the channel.

7. The system of claim 1, wherein the peristaltic pump further comprises a guide member having a plurality of recesses, each of the plurality of rollers positioned in a respective one of the plurality of recesses.

8. The system of claim 1, wherein the probe further comprises a motor disposed within the housing, the motor having a motor shaft coupled to the roller driver.

9. The system of claim 8, wherein the motor rotates the roller driver.

10. The system of claim 1, wherein the roller is spherical.

11. The system of claim 1, wherein the deformable conduit comprises a first segment carrying the material in a first direction and a second segment carrying the material in a second direction.

* * * * *

UNITED STATES PATENT AND TRADEMARK OFFICE
CERTIFICATE OF CORRECTION

| | |
|---|---|
| PATENT NO. | : 10,690,127 B2 |
| APPLICATION NO. | : 15/253046 |
| DATED | : June 23, 2020 |
| INVENTOR(S) | : Francisco Javier Ochoa |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 592 days.

Signed and Sealed this
Fourteenth Day of February, 2023

Katherine Kelly Vidal
*Director of the United States Patent and Trademark Office*